(12) United States Patent  (10) Patent No.: US 8,637,079 B2
Nakamura et al.  (45) Date of Patent: Jan. 28, 2014

(54) SOLID PREPARATION COMPRISING ALOGLIPTIN AND PIOGLITAZONE

(75) Inventors: Kenji Nakamura, Osaka (JP); Kenichiro Kiyoshima, Osaka (JP); Junya Nomura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 359 days.

(21) Appl. No.: 12/449,255

(22) PCT Filed: Jan. 30, 2008

(86) PCT No.: PCT/JP2008/051900
§ 371 (c)(1),
(2), (4) Date: Jul. 30, 2009

(87) PCT Pub. No.: WO2008/093882
PCT Pub. Date: Aug. 7, 2008

(65) Prior Publication Data
US 2010/0092551 A1   Apr. 15, 2010

(30) Foreign Application Priority Data

Feb. 1, 2007   (JP) ................................. 2007-023594

(51) Int. Cl.
*A61K 9/24*   (2006.01)
*A61K 9/20*   (2006.01)
*A61K 9/26*   (2006.01)

(52) U.S. Cl.
USPC ........... 424/472; 424/464; 424/465; 424/469; 424/470

(58) Field of Classification Search
USPC .......................... 424/464, 465, 469, 470, 472
See application file for complete search history.

(56) References Cited

U.S. PATENT DOCUMENTS

| | | | |
|---|---|---|---|
| 4,687,777 A | 8/1987 | Meguro et al. |
| 5,965,584 A | 10/1999 | Ikeda et al. |
| 6,030,641 A | 2/2000 | Yamashita et al. |
| 6,150,383 A | 11/2000 | Ikeda et al. |
| 6,150,384 A | 11/2000 | Ikeda et al. |
| 6,166,042 A | 12/2000 | Ikeda et al. |
| 6,166,043 A | 12/2000 | Ideda et al. |
| 6,172,090 B1 | 1/2001 | Ikeda et al. |
| 6,211,205 B1 | 4/2001 | Ikeda et al. |
| 6,271,243 B1 | 8/2001 | Ikeda et al. |
| 6,303,640 B1 | 10/2001 | Ikeda et al. |
| 6,329,404 B1 | 12/2001 | Ikeda et al. |
| 6,660,716 B1 | 12/2003 | Yakubu-Madus et al. |
| 7,125,873 B2 | 10/2006 | Edmondson et al. |
| 7,700,128 B2 | 4/2010 | Doken et al. |
| 2003/0166578 A1 | 9/2003 | Arch et al. |
| 2005/0261271 A1 | 11/2005 | Feng et al. |
| 2006/0141128 A1 | 6/2006 | Ohkouchi et al. |
| 2006/0204578 A1 | 9/2006 | Vergez et al. |
| 2006/0205675 A1 | 9/2006 | Arch et al. |
| 2006/0223870 A1 | 10/2006 | Doken et al. |
| 2006/0286168 A1 | 12/2006 | Koike et al. |
| 2009/0042863 A1 | 2/2009 | Takeuchi et al. |

FOREIGN PATENT DOCUMENTS

| | | |
|---|---|---|
| AU | 8532798 A | 12/1998 |
| DE | 19725911 A1 | 12/1998 |
| JP | 11-049668 A | 2/1999 |
| JP | 2000-154137 A | 6/2000 |
| JP | 2005-154418 A | 6/2005 |
| WO | WO 92/09273 A1 | 6/1992 |
| WO | WO 98/56359 A2 | 12/1998 |
| WO | WO 00/16776 A1 | 3/2000 |
| WO | WO 01/35941 A2 | 5/2001 |
| WO | WO 01/52825 A2 | 7/2001 |
| WO | WO 01/68603 A2 | 9/2001 |
| WO | WO 02/083128 A1 | 10/2002 |
| WO | WO 03/004498 A1 | 1/2003 |
| WO | WO 2004/045608 A1 | 6/2004 |
| WO | WO 2005/067976 A2 | 7/2005 |
| WO | WO 2005/095381 A1 | 10/2005 |
| WO | WO 2006/047248 A1 | 5/2006 |
| WO | WO 2006/135693 A2 | 12/2006 |
| WO | WO 2007/033266 A2 | 3/2007 |
| WO | WO 2007/035372 A2 | 3/2007 |
| WO | WO 2007/072992 A2 | 6/2007 |

OTHER PUBLICATIONS

Opposition filed Jul. 16, 2010, against corresponding Colombian application, 9 pages.
Published protocol entitled "Placebo-Controlled Study of the Combination of SYR-322 and Pioglitazone HCI in the Treatment of Type 2 Diabetes," May 23, 2006, 1 page.
Clinical Trial: "Placebo-Controlled Study of the Combination of SYR-322 and Pioglitazone HCI in the Treatment of Type 2 Diabetes," Study start Apr. 2006, 7 pages.
Clinical Trial: "Study of SYR-322 Combined with Pioglitazone in the Treatment of Type 2 Diabetes," Study start Jan. 2006, 7 pages.
Zarate et al., "Gliptins as an Advance in the Antidiabetic Drugs Therapy," Acta Medica Grupo Angeles, Oct.-Dec. 2006, 4(4):263, with English translation, 4 pages.
Approval of Sitagliptin for Diabetes Mellitus Type 2, Dec. 27, 2006, www.pmfarma.es/noticias/6792-aprobacion-de-la-sitagliptina-para-la-diabetes-mellitus-tipo-2.html, with English translation, 2 pages.
Krentz et al., "Anti-diabetic treatment in obese patients with type-2 diabetes-effects of medication on body weight," US Endocrine Disease, 2006, 1-8.

(Continued)

*Primary Examiner* — Rachael E Bredefeld
(74) *Attorney, Agent, or Firm* — Foley & Lardner LLP

(57) ABSTRACT

A solid preparation containing compound (I), wherein the definition of compound (I) is as defined in the description, and pioglitazone, which is useful as a therapeutic drug for diabetes and the like and superior in the dissolution property, chemical stability and dissolution stability, is provided. A solid preparation containing the following first and second parts:
(1) the first part containing compound (I) or a salt thereof and, as the first excipient, sugar or sugar alcohol; and
(2) the second part containing pioglitazone or a salt thereof and, as the second excipient, sugar or sugar alcohol.

4 Claims, No Drawings

(56) References Cited

OTHER PUBLICATIONS

"Efficacy of Alogliptin With Pioglitazone (Actos®) in Subjects with Type 2 Diabetes Mellitus," ClinicalTrials.gov http://clinicaltrials.gov/ct2/show/NCT00395512, last updated Nov. 29, 2011, 5 pages.

Aulton, Michael E., Ed., Pharmaceutics: The Science of Dosage Form Design, $2^{nd}$ Edition (Spanish Edition), 2002, 327-328, with English translation, 2 pages.

Aulton, Michael E., Ed., Pharmaceutics: The Science of Dosage Form Design, $2^{nd}$ Edition (Spanish Edition), 2002, p. 405 excerpt.

The Merck Index, $12^{th}$ Edition, 1996, 913 and 979.

Goodman and Gilman, The Pharmacological Basis of Therapeutics, $11^{th}$ Ed., McGraw-Hill Interamericana, p. 1639 (Spanish version), with English translation, 4 pages, 2006.

Guedas et al., Pharmaceutical Technology, $4^{th}$ Edition, Editorial Acribia Zaragoza (Spain), excerpt from pp. 55, 56, 298, 328, 1981.

SOLID PREPARATION COMPRISING ALOGLIPTIN AND PIOGLITAZONE

TECHNICAL FIELD OF THE INVENTION

The present invention relates to a solid preparation comprising 2-[[6-[(3R)-3-amino-1-piperidinyl]-3,4-dihydro-3-methyl-2,4-dioxo-1(2H)-pyrimidinyl]methyl]-benzonitrile (general name: Alogliptin; hereinafter sometimes to be referred to as compound (I)) or a salt thereof, and pioglitazone or a salt thereof, which is useful as a therapeutic drug for diabetes and the like.

BACKGROUND OF THE INVENTION

Compound (I) to be used in the present invention is reported as an inhibitor of dipeptidyl peptidase (DPP-IV), which is an enzyme that decomposes glucagon-like peptide-1 (GLP-1), which is a hormone enhancing insulin secretion (patent reference 1).

However, a preparation comprising compound (I) or a salt thereof and pioglitazone or a salt thereof has not been reported.

[patent reference 1] US-B-2005/0261271

DISCLOSURE OF THE INVENTION

Compound (I), which is a DPP-IV inhibitor, and pioglitazone are both effective for the treatment of diabetes and the like, and provision of a preparation (combination agent) containing them as active ingredients provides extremely high usefulness from the clinical aspect. However, practicalization of a preparation containing plural active ingredients is not easy as compared to a preparation containing a single active ingredient. For example, since the dissolution rate of an active ingredient from a preparation can influence the time-course drug efficacy profile after administration, practicalization of a preparation requires control of the preparation formulation to optimize the dissolution rate of the active ingredient. In the case of a combination agent, however, it is associated with high difficulty from the aspect of pharmaceutical technology since the dissolution rate of each active ingredient needs to be optimized. Moreover, it is also necessary to suppress an adverse influence (degraded storage or chemical stability such as time-course decomposition of active ingredients, decreased activity and the like, degraded dissolution stability such as time-course changes in the active ingredient dissolution pattern and the like, and the like) caused by the interaction of plural active ingredients contained in a combination agent.

The present inventors have conducted intensive studies in an attempt to solve the above-mentioned problems and found that, by individually preparing the first part containing compound (I) or a salt thereof and, as the first excipient, sugar or sugar alcohol, and the second part containing pioglitazone or a salt thereof and, as the second excipient, sugar or sugar alcohol, and forming a solid preparation containing these two parts, the dissolution rate of each active ingredient can be controlled, and an adverse influence caused by the interaction of the respective active ingredients can be suppressed, and further study has resulted in the completion of the present invention.

Accordingly, the present invention relates to

[1] a solid preparation comprising the following first and second parts:
(1) the first part comprising compound (1) or a salt thereof and, as the first excipient, sugar or sugar alcohol; and
(2) the second part comprising pioglitazone or a salt thereof and, as the second excipient, sugar or sugar alcohol,
[2] the solid preparation of the above-mentioned [1], wherein the sugar or sugar alcohol is lactose, sucrose, erythritol or mannitol,
[3] the solid preparation of the above-mentioned [2], wherein the first and the second excipients are mannitol,
[4] the solid preparation of the above-mentioned [3], which is a coated tablet comprising an inner core made of the first part, and an outer layer made of the second part,
[5] the solid preparation of the above-mentioned [2], wherein the first excipient is mannitol and the second excipient is lactose,
[6] the solid preparation of the above-mentioned [5], which is a coated tablet comprising an inner core made of the second part, and an outer layer made of the first part,
[7] the solid preparation of the above-mentioned [5], which is a multi-layer tablet comprising the first layer made of the first part, and the second layer made of the second part, and the like.

The solid preparation of the present invention is useful as a therapeutic drug for diabetes and the like, can optimize the dissolution rate of the active ingredient contained in the preparation and can suppress an adverse influence (degraded storage or chemical stability such as time-course decomposition of active ingredients, decreased activity and the like, degraded dissolution stability such as time-course changes in the active ingredient dissolution pattern and the like, and the like) caused by the interaction of active ingredients contained in the preparation.

DETAILED DESCRIPTION OF THE INVENTION

The solid preparation of the present invention is explained in detail in the following.

The first and the second parts in the solid preparation of the present invention mean compositions or constituent components each capable of existing as an independent composition.

(1) First Part

The first part in the present invention is a part (composition) containing compound (I) or a salt thereof and, as the first excipient, sugar or sugar alcohol.

In the present specification, the "sugar or sugar alcohol" to be used as the first excipient is sometimes to be abbreviated simply as "the first excipient".

Examples of the salt of compound (I) include a pharmacologically acceptable salt, such as a salt with inorganic acid, a salt with organic acid, a salt with basic or acidic amino acid and the like.

Preferable examples of the salt with inorganic acid include salts with hydrochloric acid, hydrobromic acid, nitric acid, sulfuric acid, phosphoric acid and the like.

Preferable examples of the salt with organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Preferable examples of the salt of compound (I) include salts with benzoic acid, trifluoroacetic acid, p-toluenesulfonic acid and the like, more preferably a salt with benzoic acid.

Compound (I) or a salt thereof is preferably benzoate of compound (I), trifluoroacetate of compound (I), or p-toluenesulfonate of compound (I), more preferably benzoate of compound (I) (sometimes to be abbreviated as compound (IA) in the present specification).

The content of compound (I) or a salt thereof is preferably 0.1-90 parts by weight, more preferably 0.5-80 parts by weight, still more preferably 1-70 parts by weight, relative to 100 parts by weight of the first part in the present invention.

Examples of the sugar in the first excipient include lactose, sucrose, fructose, glucose and the like, preferably, lactose or sucrose.

Examples of the sugar alcohol in the first excipient include erythritol, mannitol, sorbitol, xylitol, maltitol and the like, preferably, erythritol or mannitol, more preferably mannitol.

These sugar and sugar alcohol may be used alone, or two or more kinds thereof may be used in combination.

The first excipient is preferably lactose, sucrose, erythritol or mannitol, more preferably mannitol.

The amount of the first excipient to be used in the present invention is preferably 5-99 parts by weight, more preferably 10-95 parts by weight, still more preferably 20-90 parts by weight, relative to 100 parts by weight of the above-mentioned first part.

The weight ratio of compound (I) or a salt thereof relative to the first excipient (compound (I) or a salt thereof:first excipient) is preferably 0.001-15:1, more preferably 0.005-10:1, still more preferably 0.01-5:1.

The above-mentioned first part may have any shape or size as long as it can form a solid preparation together with the below-mentioned second part, and can be administered (preferably orally administered) to living organisms. In addition, the first part may have any inside structure, and the inside may be uniform or nonuniform.

The above-mentioned first part may further contain an additive conventionally used in the field of pharmaceutical preparation. Examples of the additive include excipients other than sugar or sugar alcohol, disintegrant, binder, lubricant, colorant, pH adjusting agent, surfactant, stabilizer, acidulant, flavor, glidant, coating base, coating additive and the like. Unless particularly indicated, these additives are used in an amount conventionally employed in the field of pharmaceutical preparation.

The above-mentioned first part can be produced by mixing compound (I) or a salt thereof and the first excipient and, where necessary, the above-mentioned additive according to a method known per se and then, according to a dosage form, compression molding or covering the second part.

Preferable examples of the excipient other than sugar or sugar alcohol include starches such as corn starch, potato starch, wheat starch, rice starch, partly pregelatinized starch, pregelatinized starch, porous starch and the like; anhydrous calcium phosphate, crystalline cellulose (e.g., microcrystalline cellulose), precipitated calcium carbonate, calcium silicate and the like. Of these, crystalline cellulose is preferable.

The amount of the excipient other than sugar or sugar alcohol is preferably 1-40 parts by weight, more preferably 5-30 parts by weight, still more preferably 10-20 parts by weight, relative to 100 parts by weight of the above-mentioned first part.

Preferable examples of the disintegrant include carboxymethylcellulose, calcium carboxymethylcellulose, sodium carboxymethyl starch, croscarmellose sodium, croscarmellose calcium, crospovidone, low-substituted hydroxypropylcellulose, hydroxypropyl starch and the like. Of these, croscarmellose sodium is preferable.

The amount of the disintegrant to be used is preferably 0.1-30 parts by weight, more preferably 1-20 parts by weight, still more preferably 2-10 parts by weight, relative to 100 parts by weight of the above-mentioned first part.

Preferable examples of the binder include crystalline cellulose (e.g., microcrystalline cellulose), hydroxypropylcellulose [e.g., grades: L, SL, SL-T, SSL (trade name); Nippon Soda Co., Ltd.], hydroxypropylmethylcellulose [e.g., TC-5 (grades: MW, E, EW, R, RW) (trade name); Shin-Etsu Chemical Co., Ltd.], polyvinylpyrrolidone, gum arabic and the like. Of these, hydroxypropylcellulose is preferable.

The amount of the binder to be used is preferably 0.1-40 parts by weight, more preferably 0.5-30 parts by weight, still more preferably 1-20 parts by weight, relative to 100 parts by weight of the above-mentioned first part.

Preferable examples of the lubricant include magnesium stearate, calcium stearate, talc, sucrose esters of fatty acids, sodium stearyl fumarate and the like. Of these, magnesium stearate is preferable.

The amount of the lubricant to be used is preferably 0.01-5 parts by weight, more preferably 0.05-3 parts by weight, still more preferably 0.1-2 parts by weight, relative to 100 parts by weight of the above-mentioned first part.

Preferable examples of the colorant include food colors such as Food Color Yellow No. 5, Food Color Red No. 2, Food Color Blue No. 2 and the like, food lake colors, red ferric oxide (diiron trioxide), yellow ferric oxide and the like.

Preferable examples of the pH adjusting agent include citric acid or a salt thereof, phosphoric acid or a salt thereof, carbonic acid or a salt thereof, tartaric acid or a salt thereof, fumaric acid or a salt thereof, acetic acid or salt thereof, amino acid or a salt thereof and the like.

Preferable examples of the surfactant include sodium lauryl sulfate, polysorbate 80, polyoxyethylene(160)polyoxypropylene(30)glycol and the like.

Preferable examples of the stabilizer include tocopherol, tetrasodium edetate, nicotinic acid amide, cyclodextrins and the like.

Preferable examples of the acidulant include ascorbic acid, citric acid, tartaric acid, malic acid and the like.

Preferable examples of the flavor include menthol, peppermint oil, lemon oil, vanillin and the like.

Preferable examples of the glidant include light anhydrous silicic acid, hydrated silicon dioxide, talc and the like.

Preferable examples of the coating base include sugar coating base, aqueous film coating base, enteric film coating base, sustained-release film coating base and the like.

As the sugar coating base, sucrose is used. Furthermore, one or more kinds selected from talc, precipitated calcium carbonate, gelatin, gum arabic, pullulan, carnauba wax and the like may be used in combination.

Examples of the aqueous film coating base include cellulose polymers such as hydroxypropylcellulose [e.g., grades: L, SL, SL-T, SSL (trade name); Nippon Soda Co., Ltd.], hydroxypropylmethylcellulose [e.g., TC-5 (grades: MW, E, EW, R, RW) (trade name); Shin-Etsu Chemical Co., Ltd.], hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; polysaccharides such as pullulan and the like, and the like.

Examples of the enteric film coating base include cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like.

Examples of the sustained-release film coating base include cellulose polymers such as ethylcellulose and the like; acrylic acid polymers such as aminoalkyl methacrylate copolymer RS [Eudragit RS (trade name)], ethyl acrylate•methacrylic acid methyl copolymer suspension [Eudragit NE (trade name)] and the like; and the like.

Preferable examples of the coating additive include light shielding agents such as titanium dioxide and the like, fluidizers such as talc and the like, and/or colorants such as red ferric oxide (diiron trioxide), yellow ferric oxide and the like; plasticizers such as polyethylene glycol [e.g., macrogol 6000 (trade name)], triethyl citrate, castor oil, polysorbates and the like; organic acids such as citric acid, tartaric acid, malic acid, ascorbic acid and the like; and the like.

The above-mentioned additive may be a mixture of two or more kinds at an appropriate ratio.

The above-mentioned first part preferably contains compound (I) or a salt thereof (preferably benzoate of compound (I)); the first excipient (preferably mannitol); an excipient other than sugar and sugar alcohol (preferably crystalline cellulose); a disintegrant (preferably croscarmellose sodium); a binder (preferably hydroxypropylcellulose); and a lubricant (preferably magnesium stearate).

(2) Second Part

The second part in the present invention is a part (composition) containing pioglitazone or a salt thereof and, as the second excipient, sugar or sugar alcohol.

In the present specification, the "sugar or sugar alcohol" to be used as the second excipient is sometimes to be simply abbreviated as "the second excipient".

Examples of the salt of pioglitazone include pharmacologically acceptable salts such as salts with inorganic acids, salts with organic acids, salts with basic or acidic amino acids and the like. As such salt, those recited as the examples of the salt of the above-mentioned compound (I) can be used.

Preferable examples of the salt of pioglitazone include salts with hydrochloric acid.

As pioglitazone or a salt thereof, pioglitazone hydrochloride is preferable.

The content of the pioglitazone or a salt thereof is preferably 0.1-60 parts by weight, more preferably 1-50 parts by weight, more preferably 2-40 parts by weight, relative to 100 parts by weight of the above-mentioned second part.

As the sugar and sugar alcohol in the second excipient, those recited as the examples of the sugar and sugar alcohol of the above-mentioned first excipient can be used respectively.

The second excipient is preferably lactose, sucrose, erythritol or mannitol, more preferably lactose or mannitol.

The amount of the second excipient to be used in the present invention is preferably 5-99 parts by weight, more preferably 10-95 parts by weight, still more preferably 20-90 parts by weight, relative to 100 parts by weight of the above-mentioned second part.

The weight ratio of the pioglitazone or a salt thereof relative to the second excipient (pioglitazone or a salt thereof: second excipient) is preferably 0.001-30:1, more preferably 0.005-10:1, still more preferably 0.01-1:1.

The above-mentioned second part may have any shape or size as long as it can form a solid preparation together with the aforementioned first part, and can be administered (preferably orally administered) to living organisms. In addition, the second part may have any inside structure, and the inside may be uniform or nonuniform.

The above-mentioned second part may further contain an additive conventionally used in the field of pharmaceutical preparation, and can be produced according to a known method. Examples of the additive include those recited in the above-mentioned first part (e.g., excipients other than sugar and sugar alcohol, disintegrant, binder, lubricant, colorant, pH adjusting agent, surfactant, stabilizer, acidulant, flavor, fluidizer, coating base, coating additive and the like). Unless particularly indicated, these additives are used in an amount conventionally employed in the field of pharmaceutical preparation.

The above-mentioned second part can be produced by mixing pioglitazone or a salt thereof and the second excipient and, where necessary, the above-mentioned additive according to a method known per se and then, according to a dosage form, compression molding or covering the first part.

The amount of the excipient other than sugar and sugar alcohol to be used in the second part is preferably 0.1-40 parts by weight, more preferably 0.1-30 parts by weight, still more preferably 0.1-20 parts by weight, relative to 100 parts by weight of the above-mentioned second part.

The amount of the disintegrant to be used in the second part is preferably 0.1-30 parts by weight, more preferably 1-20 parts by weight, still more preferably 2-10 parts by weight, relative to 100 parts by weight of the above-mentioned second part.

The amount of the binder to be used in the second part is preferably 0.1-30 parts by weight, more preferably 0.5-20 parts by weight, still more preferably 1-10 parts by weight, relative to 100 parts by weight of the above-mentioned second part.

The amount of the lubricant to be used in the second part is preferably 0.01-5 parts by weight, more preferably 0.05-1 parts by weight, still more preferably 0.1-0.5 parts by weight, relative to 100 parts by weight of the above-mentioned second part.

The amount of other additives to be used in the second part is the amount conventionally used in the field of pharmaceutical preparation.

The above-mentioned second part preferably contains pioglitazone or a salt thereof (preferably pioglitazone hydrochloride); the second excipient (preferably lactose or mannitol); and a binder (preferably hydroxypropylcellulose).

The weight ratio of the second part relative to the first part of the solid preparation of the present invention (second part: first part) is preferably 0.01-100:1, more preferably 0.05-10:1, still more preferably 0.1-5:1.

The compound (I) and pioglitazone may be solvates (e.g., hydrates) or non-solvates.

In addition, compound (I) may be labeled with an isotope (e.g. $^3H$, $^{14}C$, $^{35}S$, $^{125}I$).

Furthermore, it may be a deuterium converter wherein $^1H$ is converted to $^2H(D)$.

The solid preparation of the present invention is not particularly limited as long as it is a preparation wherein the first part and the second part are integrally formed, and can be produced by mixing these parts together with, where necessary, the above-mentioned additives according to a method known per se, followed by compression molding, or covering one part with the other part.

In addition, the solid preparation of the present invention may have an inactive intermediate layer between the first part and the second part.

When the solid preparation of the present invention has an intermediate layer, the intermediate layer is formed at the ratio of preferably 0.1-1000 parts by weight, more preferably 0.5-500 parts by weight, still more preferably 1-200 parts by weight, relative to 100 parts by weight of the first part.

When the solid preparation of the present invention has such an intermediate layer, an adverse influence (degraded storage or chemical stability such as time-course decomposition of active ingredients, decreased activity and the like, degraded dissolution stability such as time-course changes in the active ingredient dissolution pattern and the like, and the like) caused by the interaction of active ingredients can be suppressed more effectively.

Specific examples of the solid preparation of the present invention include [1] a coated tablet containing the inner core made of the first part and the outer layer made of the second part (sometimes to be abbreviated as "coated tablet (A)" in the present specification); [2] a coated tablet containing the inner core made of the second part and the outer layer made of the first part (sometimes to be abbreviated as "coated tablet (B)" in the present specification); and [3] a multi-layer tablet containing the first layer made of the first part and the second layer made of the second part (sometimes to be abbreviated as "multi-layer tablet (A)" in the present specification).

In the above-mentioned coated tablet (A), the first and the second excipients are both preferably mannitol.

The coated tablet (A) of the present invention can be produced, for example, by the following production steps.

The inner core made of the first part can be produced, for example, by granulating compound (I) or a salt thereof and the first excipient together with, where necessary, an additive. After granulation, an operation such as drying, sizing, and the like may be performed as necessary.

The additive preferably includes excipients other than sugar and sugar alcohol (preferably crystalline cellulose); disintegrants (preferably croscarmellose sodium); binders (preferably hydroxypropylcellulose); and lubricants (preferably magnesium stearate) and the like.

The inner core made of the above-mentioned first part can be preferably produced by the following production steps.
1) compound (I) or a salt thereof (preferably benzoate of compound (I)); the first excipient (preferably mannitol); and excipients other than sugar and sugar alcohol (preferably crystalline cellulose) are granulated using a dispersion liquid of a binder (preferably hydroxypropylcellulose) in a solvent (e.g., water, acetone, ethyl alcohol, propyl alcohol, and a mixture of these at an appropriate ratio; preferably water).

Here, the dispersion liquid may be any of solution and suspension, and the "dispersion liquid" in the present specification includes both solution and suspension.
2) The obtained granules are dried, sized and the obtained milled granule, a disintegrant (preferably croscarmellose sodium), a lubricant (preferably magnesium stearate) and, where necessary, an excipient other than sugar and sugar alcohol (preferably crystalline cellulose) are mixed.
3) The obtained mixture is compression molded (preferably tableted).

On the other hand, the outer layer made of the second part can be produced, for example, by applying pioglitazone or a salt thereof and the second excipient together with, where necessary, an additive to the above-mentioned first part.

The applying can be performed, for example, by compression molding, coating and the like. The additive is preferably a binder (preferably hydroxypropylcellulose) and the like.

The above-mentioned outer layer made of the second part can be preferably produced according to the following production steps.
1) The inner core made of the first part is coated with a dispersion liquid of pioglitazone or a salt thereof (preferably pioglitazone hydrochloride), the second excipient (preferably mannitol) and a binder (preferably hydroxypropylcellulose) in a solvent (e.g., water, acetone, ethyl alcohol, propyl alcohol, and a mixture of these at an appropriate ratio; preferably water).

During production of coated tablet (A), it is preferable to form an inactive intermediate layer between an inner core and an outer layer to avoid a direct contact of them. The intermediate layer contains, for example, the above-mentioned coating base and a coating additive. The intermediate layer preferably contains an aqueous film coating base (preferably hydroxypropylmethylcellulose) and a glidant (preferably talc).

In the above-mentioned coated tablet (A), the outer layer is formed in a proportion of preferably 0.1-1000 parts by weight, more preferably 1-300 parts by weight, still more preferably 10-100 parts by weight, relative to 100 parts by weight of the inner core.

In the above-mentioned coated tablet (A), moreover, the intermediate layer is formed in a proportion of preferably 0.1-30 parts by weight, more preferably 0.5-20 parts by weight, still more preferably 1-10 parts by weight, relative to 100 parts by weight of the inner core.

In the above-mentioned coated tablet (B), the first excipient is preferably mannitol and the second excipient is preferably lactose.

The above-mentioned coated tablet (B) can be produced in the same manner as coated tablet (A) except that the second part is used as the inner core and the first part is used as the outer layer.

In the above-mentioned coated tablet (B), the outer layer is formed in a proportion of preferably 1-300 parts by weight, more preferably 5-200 parts by weight, still more preferably 10-80 parts by weight, relative to 100 parts by weight of the inner core.

In the above-mentioned multi-layer tablet (A), the first excipient is preferably mannitol and the second excipient is preferably lactose.

Multi-layer tablet (A) can be produced, for example, according to the following production steps.

The first layer is produced by mixing compound (I) or a salt thereof and the first excipient and, where necessary, an additive, and granulating the obtained mixture. After granulation, an operation such as drying, sizing, and the like may be performed as necessary.

Then, pioglitazone or a salt thereof and the second excipient are mixed with an additive as necessary, and the obtained mixture is superimposed to form a layer on the above-mentioned first layer, which is followed by compression molding (preferably tableting).

In this case, an inactive intermediate layer may be formed between respective layers to avoid a direct contact of them. The intermediate layer contains, for example, the above-mentioned binder.

Multi-layer tablet (A) can be produced, for example, according to the following production steps.
1) Compound (I) or a salt thereof (preferably benzoate of compound (I)); the first excipient (preferably mannitol); and an excipient other than sugar and sugar alcohol (preferably crystalline cellulose) are granulated with a dispersion liquid of a binder (preferably hydroxypropylcellulose) in a solvent (e.g., water, acetone, ethyl alcohol, propyl alcohol, and a mixture of these at an appropriate ratio; preferably water).
2) The obtained granules are dried, sized, and the obtained milled granule and a disintegrant (preferably croscarmellose sodium), a lubricant (preferably magnesium stearate) and, as necessary, an excipient other than sugar and sugar alcohol (preferably crystalline cellulose) are mixed to give granules.

3-1) Pioglitazone or a salt thereof (preferably pioglitazone hydrochloride); the second excipient (preferably lactose); and a disintegrant (preferably croscarmellose sodium) are granulated with a dispersion liquid of a binder (preferably hydroxypropylcellulose) in a solvent (e.g., water, acetone, ethyl alcohol, propyl alcohol, and a mixture of these at an appropriate ratio; preferably water).

3-2) The obtained granules are further granulated with a dispersion liquid of a binder (preferably hydroxypropylcellulose) and the second excipient (preferably lactose) in a solvent (e.g., water, acetone, ethyl alcohol, propyl alcohol, and a mixture of these at an appropriate ratio; preferably water).

4) The obtained granules are dried, sized, and the obtained milled granule and a disintegrant (preferably croscarmellose sodium) and a lubricant (preferably magnesium stearate) are mixed to give granules.

5) The granules obtained in the above-mentioned 4) and the granules in the above-mentioned 2) are superimposed on each other in layers, followed by compression molding (preferably tableting).

The dispersion in the above-mentioned steps may be any of solution and suspension.

The step of the above-mentioned 3-2) is particularly important to control the dissolution rate of each active ingredient and suppress an adverse influence caused by an interaction of the active ingredients.

In the above-mentioned multi-layer tablet (A), the second layer is formed in a proportion of preferably 1-1000 parts by weight, more preferably 5-500 parts by weight, still more preferably 10-300 parts by weight, relative to 100 parts by weight of the first layer.

In the above-mentioned multi-layer tablet (A), moreover, the intermediate layer is formed in a proportion of preferably 0.1-1000 parts by weight, more preferably 0.5-500 parts by weight, still more preferably 1-200 parts by weight, relative to 100 parts by weight of the first layer.

A capsule produced by filling the above-mentioned coated tablet (A) or (B) or multi-layer tablet (A) in a capsule (e.g., gelatin capsule) is also encompassed in the solid preparation of the present invention.

The solid preparation of the present invention is preferably coated tablet (A) or multi-layer tablet (A), more preferably multi-layer tablet (A).

In addition, a film coating preparation produced by film coating the above-mentioned coated tablet (A), (B) or multi-layer tablet (A) with the above-mentioned coating agent and coating additive is also encompassed in the solid preparation of the present invention.

In addition, the solid preparation of the present invention may be stamped or printed with letters for discrimination, or have a separating line for dividing the tablet.

From the aspects of easy administration, preparation strength and the like, the solid preparation of the present invention is preferably film-coated.

The operations such as mixing, compression molding, coating and the like in the aforementioned production step are performed according to a method conventionally used in the technical field of pharmaceutical preparations.

The mixing is performed, for example, using a mixer such as a V-type mixer, a tumbler mixer and the like; and a granulation machine such as a high speed mixer granulator, a fluid bed granulator, an extrusion granulator, a roller compactor and the like.

Compression molding is performed, for example, using a single punch tableting machine, a rotary tableting machine and the like.

When a single punch tableting machine, a rotary tableting machine and the like are used, a tableting pressure of generally 1-35 kN/cm$^2$ (preferably 5-35 kN/cm$^2$) is preferably employed. Furthermore, to prevent capping, a tapered die is preferably used.

The coating is performed, for example, using a film coating apparatus and the like.

The solid preparation of the present invention can be safely administered orally or parenterally to a mammal (e.g., mouse, rat, rabbit, cat, dog, bovine, horse, monkey, human).

The solid preparation of the present invention and each active ingredient contained in the solid preparation are useful for the prophylaxis or treatment of, for example, diabetes [e.g., type 1 diabetes, type 2 diabetes, type 1.5 diabetes (LADA (Latent Autoimmune Diabetes in Adults)), gestational diabetes, diabetes with impaired insulin secretion, obese diabetes, impaired glucose tolerance (IGT), IFG (Impaired Fasting Glucose), IFG (Impaired Fasting Glycaemia)], diabetic complications [e.g., neuropathy, nephropathy, retinopathy, cataract, macroangiopathy, arteriosclerosis, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, cerebrovascular disorder, peripheral blood circulation disorder], obesity, hyperlipidemia (e.g., hypertriglyceridemia, hypercholesterolemia, hypoHDL-emia, postprandial hyperlipemia), arteriosclerosis (e.g., atherosclerosis), hypertension, myocardial infarction, angina pectoris, cerebrovascular disorder (e.g., cerebral infarction, cerebral apoplexy), insulin resistance syndrome, syndrome X, dysmetabolic syndrome and the like. In addition, the solid preparation of the present invention is also useful for secondary prevention of the above-mentioned various diseases (e.g., secondary prevention of cardiovascular event such as myocardial infarction and the like) or suppression of progression [e.g., suppression of progression from impaired glucose tolerance to diabetes; suppression of progression from diabetes to diabetic complications (preferably diabetic neuropathy, diabetic nephropathy, diabetic retinopathy, arteriosclerosis)].

The dose of the solid preparation of the present invention only needs to be an effective amount of compound (I) or pioglitazone contained in the solid preparation.

Here, the effective amount of compound (I) or a salt thereof is, for example, generally 1-1000 mg/day, preferably 1-100 mg/day, more preferably 10-30 mg/day, even more preferably 12.5-25 mg/day, as compound (I) (free form) for one adult (body weight 60 kg).

In the case of pioglitazone or a salt thereof, the effective amount thereof is generally 5-100 mg/day, preferably 7.5-60 mg/day, more preferably 15-60 mg/day, as pioglitazone (free form) for one adult (body weight 60 kg).

The solid preparation of the present invention is preferably administered to the aforementioned mammal 1 to 3 times, more preferably once, relative to day. Particularly, the solid preparation of the present invention is preferably administered once before breakfast to a mammal.

Particularly preferable specific examples of the solid preparation of the present invention include "coated tablet containing pioglitazone hydrochloride (outer layer) 16.53 mg (15 mg as pioglitazone) and benzoate of compound (I) (inner core) 17 mg (12.5 mg as compound (I)) per one tablet";

"coated tablet containing pioglitazone hydrochloride (outer layer) 33.06 mg (30 mg as pioglitazone) and benzoate of compound (I) (inner core) 17 mg (12.5 mg as compound (I)) per one tablet";

"coated tablet containing pioglitazone hydrochloride (outer layer) 49.59 mg (45 mg as pioglitazone) and benzoate of compound (I) (inner core) 17 mg (12.5 mg as compound (I)) per one tablet";
"coated tablet containing pioglitazone hydrochloride (outer layer) 16.53 mg (15 mg as pioglitazone) and benzoate of compound (I) (inner core) 34 mg (25 mg as compound (I)) per one tablet";
"coated tablet containing pioglitazone hydrochloride (outer layer) 33.06 mg (30 mg as pioglitazone) and benzoate of compound (I) (inner core) 34 mg (25 mg as compound (I)) per one tablet";
"coated tablet containing pioglitazone hydrochloride (outer layer) 49.59 mg (45 mg as pioglitazone) and benzoate of compound (I) (inner core) 34 mg (25 mg as compound (I)) per one tablet";
"coated tablet containing pioglitazone hydrochloride (inner core) 49.59 mg (45 mg as pioglitazone) and benzoate of compound (I) (outer layer) 68 mg (50 mg as compound (I)) per one tablet";
"multi-layer tablet containing pioglitazone hydrochloride 16.53 mg (15 mg as pioglitazone) and benzoate of compound (I) 17 mg (12.5 mg as compound (I)) per one tablet";
"multi-layer tablet containing pioglitazone hydrochloride 33.6 mg (30 mg as pioglitazone) and benzoate of compound (I) 17 mg (12.5 mg as compound (I)) per one tablet";
"multi-layer tablet containing pioglitazone hydrochloride 49.59 mg (45 mg as pioglitazone) and benzoate of compound (I) 17 mg (12.5 mg as compound (I)) per one tablet";
"multi-layer tablet containing pioglitazone hydrochloride 16.53 mg (15 mg as pioglitazone) and benzoate of compound (I) 34 mg (25 mg as compound (I)) per one tablet";
"multi-layer tablet containing pioglitazone hydrochloride 33.06 mg (30 mg as pioglitazone) and benzoate of compound (I) 34 mg (25 mg as compound (I)) per one tablet"; and
"multi-layer tablet containing pioglitazone hydrochloride 49.59 mg (45 mg as pioglitazone) and benzoate of compound (I) 34 mg (25 mg as compound (I)) per one tablet".

The solid preparation of the present invention is advantageous in the design of preparation since the dissolution rate of pioglitazone or a salt thereof from a solid preparation can be controlled by changing the kind, amount and the like of the second excipient (sugar or sugar alcohol), and/or changing the content of pioglitazone or a salt thereof.

Each of the solid preparation of the present invention and the active ingredients contained in the solid preparation can be used in combination with one or more pharmaceutical agents selected from a therapeutic agent for diabetes, a therapeutic agent for diabetic complications, a therapeutic agent for hyperlipidemia, an antihypertensive agent, an antiobesitic agent, a diuretic, an antithrombotic agent and the like (hereinafter sometimes to be abbreviated as concomitant drug).

Examples of the therapeutic agent for diabetes include insulin preparations (e.g., animal insulin preparation extracted from the pancreas of bovine or swine; human insulin preparation synthesized by genetic engineering using Escherichia coli or yeast; zinc insulin; protamine zinc insulin; fragment or derivative of insulin (e.g., INS-1), oral insulin preparation), insulin sensitizers except for pioglitazone (e.g., rosiglitazone or a salt thereof (preferably maleate), tesaglitazar, ragaglitazar, muraglitazar, edaglitazone, metaglidasen, naveglitazar, AMG-131, THR-0921), α-glucosidase inhibitors (e.g., voglibose, acarbose, miglitol, emiglitate), biguanides (e.g., metformin, buformin or salts thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors other than compound (I) (e.g., vildagliptin, sitagliptin, saxagliptin, T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., tolrestat, epalrestat, zenarestat, zopolrestat, minalrestat, fidarestat, CT-112), neurotrophic factors and increasing drugs thereof (e.g., NGF, NT-3, BDNF, neurotrophin production/secretion promoting agent described in WO01/14372 (e.g., 4-(4-chlorophenyl)-2-(2-methyl-1-imidazolyl)-5-[3-(2-methylphenoxy)propyl]oxazole)), nerve regeneration promoters (e.g., Y-128), PKC inhibitors (e.g., ruboxistaurin mesylate), AGE inhibitors (e.g., ALT946, pimagedine, N-phenacylthiazolium bromide (ALT766), ALT-711, EXO-226, pyridorin, pyridoxamine), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

Examples of the therapeutic agent for hyperlipidemia include HMG-CoA reductase inhibitors (e.g., pravastatin, simvastatin, lovastatin, atorvastatin, fluvastatin, pitavastatin, rosuvastatin or a salt thereof (e.g., sodium salt, calcium salt)), squalene synthase inhibitors (e.g., lapaquistat acetate), fibrate compounds (e.g., bezafibrate, clofibrate, simfibrate, clinofibrate), ACAT inhibitors (e.g., avasimibe, eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like.

Examples of the antihypertensive agent include angiotensin converting enzyme inhibitors (e.g., captopril, enalapril, delapril), angiotensin II receptor antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesitic agent include antiobestic agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist), pancreatic lipase inhibitors (e.g., orlistat, cetilistat), β3 agonists (e.g., AJ-9677), anorectic peptides (e.g., leptin, CNTF (ciliary neurotrophic factor)), cholecystokinin agonists (e.g., lintitript, FPL-15849), feeding deterrents (e.g., P-57) and the like.

Examples of the diuretic include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Of the above-mentioned combination drugs, insulin preparation, α-glucosidase inhibitors (preferably voglibose, acarbose), biguanides (preferably metformin hydrochloride), sulfonylureas (preferably glimepiride) are preferable.

When the solid preparation of the present invention and a concomitant drug are used in combination, the administration time of these is not limited, and the solid preparation of the present invention and the combination drug can be administered simultaneously to an administration subject, or may be administered in a staggered manner.

In addition, the solid preparation of the present invention and the concomitant drug may be administered as separate preparations to an administration subject, or the solid preparation of the present invention and the concomitant drug may be administered to an administration subject as a single preparation containing the solid preparation of the present invention and the concomitant drug.

The dose of the concomitant drug can be appropriately determined based on the clinically employed dose of each drug. In addition, the mixing ratio of the solid preparation of the present invention and the concomitant drug can be appropriately determined according to the administration subject, administration route, target disease, condition, combination and the like. For example, when the administration subject is a human, the concomitant drug may be used in an amount of 0.01 to 100 parts by weight per 1 part by weight of the solid preparation of the present invention.

Use of the concomitant drug in this way provides superior effects such as 1) enhanced action of the solid preparation of the present invention or the concomitant drug (synergistic effect of the actions of the pharmaceutical agents), 2) reduced dose of the solid preparation of the present invention or the combination drug (effect of reduction of dose of pharmaceutical agents as compared to single drug administration), 3) reduced secondary action of the solid preparation of the present invention or the concomitant drug, and the like.

The present invention is explained in more detail in the following by referring to Example, Comparative Example and Experimental Examples, which are not to be construed as limitative.

As additives for pharmaceutical preparations in the following Examples and Comparative Examples, the Japanese Pharmacopoeia 15th edition, the Japanese Pharmacopoeia Japanese Pharmaceutical Codex or Japanese Pharmaceutical Excipients 2003 compatible products were used.

EXAMPLES

Example 1

According to the formulation shown in Table 1, multi-layer tablet (A) of the present invention was produced.
(1) Hydroxypropylcellulose (grade L, Nippon Soda Co., Ltd.; 2190 g) was dissolved in purified water (34310 g) to give a binding solution (I). Compound (IA)(benzoate of compound (I); 26520 g), mannitol (32370 g) and microcrystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added microcrystalline cellulose (7250 g), croscarmellose sodium (4350 g) and magnesium stearate (725 g), and the mixture was mixed in a tumbler mixer (TM-400S, Showa Chemical Machinery) to give granule (I).
(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (20330 g), lactose (30520 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-400S, Showa Chemical Machinery) to give granule (II).
(3) Granule (I) (100 mg) and granule (II) (180 mg) were formed into a multi-layered by a rotary tableting machine (AQUA 08242L2JI, Kikusui Seisakusho) using a 8.5 mmφ punch to give a plain tablet.
(4) Hydroxypropylmethylcellulose (TC-5 RW, Shin-Etsu Chemical Co., Ltd.; 390 g) and talc (60 g) were dispersed in purified water (3500 g) to give dispersion (I). Titanium dioxide (35 g) and red ferric oxide (15 g) were dispersed in purified water (750 g) to give dispersion (II). Dispersion (II) and purified water (250 g) were added to dispersion (I), and they were mixed by stirring in a stirrer (LR400D, Yamato Scientific Co., Ltd.) to give coating solution (I). The coating solution (I) was sprayed in a coating machine (DRC-650, POWREX CORPORATION) on the plain tablet obtained in (3) until the weight of the plain tablet increased by 10 mg per one tablet to give multi-layer tablet (A) containing compound (I) (25 mg) and pioglitazone (45 mg) per one tablet.

TABLE 1

| | component | formulation amount |
|---|---|---|
| layer containing compound (I) | compound (IA) | 34 mg |
| | mannitol | 41.5 mg |
| | microcrystalline cellulose | 15 mg |
| | hydroxypropylcellulose | 2.5 mg |
| | croscarmellose sodium | 6 mg |
| | magnesium stearate | 1 mg |

TABLE 1-continued

| | component | formulation amount |
|---|---|---|
| layer containing pioglitazone | pioglitazone hydrochloride | 49.59 mg |
| | lactose | 110.43 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.7 mg |
| | red ferric oxide | 0.3 mg |

Example 2

According to the formulation shown in Table 2, the coated tablet (A) of the present invention was produced.
(1) Hydroxypropylcellulose (grade L, Nippon Soda Co., Ltd.; 2460 g) was dissolved in purified water (38540 g) to give a binding solution (I). Compound (IA) (7480 g), mannitol (50600 g) and microcrystalline cellulose (11550 g) were uniformly mixed in a fluid bed granulator (WSG-60, POWREX CORPORATION), and the mixture was granulated while spraying a binding solution (I) (33000 g) and dried to give a granule. A part of the obtained granule was pulverized with a screening mill (P-7S, Showa Chemical Machinery) and a 1.5 mmϕ punching screen to give a milled granule. To a part (67380 g) of the obtained milled granule were added croscarmellose sodium (4347 g) and magnesium stearate (724.5 g), and they were mixed in a tumbler mixer (TM-400S, Showa Chemical Machinery) to give granules. The obtained granules were tableted by a rotary tableting machine (AQUARIUS 0836SS2JII, Kikusui Seisakusho) using a 9.5 mmϕ punch at a weight of 350 mg to give plain tablet containing compound (I) (25 mg) per one tablet.
(2) Hydroxypropylmethylcellulose (TC-5 EW, Shin-Etsu Chemical Co., Ltd.; 5771 g) and talc (641.3 g) were dissolved or suspended in purified water (36340 g) to give coating solution (I). The coating solution (I) was sprayed in a coating machine (DRC-1200DS, POWREX CORPORATION) on the plain tablet obtained in (1) until the weight of the plain tablet increased by 15 mg per one tablet to give coated tablet (I).
(3) Pioglitazone hydrochloride (6360 g), hydroxypropylcellulose (grade SL-T, Nippon Soda Co., Ltd.; 384.8 g) and mannitol (12490 g) were dissolved or suspended in purified water (128200 g) to give coating solution (II). The coating solution (II) was sprayed in a coating machine (DRC-1200, POWREX CORPORATION) on the coated tablet (1) obtained in (2) until the weight of the coated tablet increased by 150 mg per one tablet to give coated tablet (II).
(4) Hydroxypropylmethylcellulose (HPMC) (TC-5 EW, Shin-Etsu Chemical Co., Ltd.; 5131 g) and macrogol 6000 (1026 g) were dissolved in purified water (30550 g) to give HPMC solution (I). Titanium dioxide (478.8 g) and red ferric oxide (205.2 g) were dispersed in purified water (8208 g) to give dispersion (I). Dispersion (I) was added to the HPMC solution (I), and they were mixed by stirring in a stirrer (MXD-2302, Satake Chemical Equipment Mfg Ltd.) to give coating solution (III). The coating solution (III) was sprayed in a coating machine (DRC-1200, POWREX CORPORATION) on the coated tablet (II) obtained in (3) until the weight of the coated tablet increased by 15 mg per one tablet to give coated tablet (A) containing compound (I) (25 mg) and pioglitazone (45 mg) per one tablet.

TABLE 2

| | component | formulation amount |
|---|---|---|
| plain tablet containing compound (I) | compound (IA) | 34 mg |
| | mannitol | 230 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 49.59 mg |
| | mannitol | 97.41 mg |
| | hydroxypropylcellulose | 3 mg |
| film coating | hydroxypropylmethylcellulose | 11.25 mg |
| | macrogol 6000 | 2.25 mg |
| | titanium dioxide | 1.05 mg |
| | red ferric oxide | 0.45 mg |

Example 3

According to the formulation shown in Table 3, the coated tablet (B) of the present invention was produced.
(1) Hydroxypropylcellulose (grade L, Nippon Soda Co., Ltd.; 450 g) was dissolved in purified water (7050 g) to give a binding solution (I). Pioglitazone hydrochloride (4959 g), lactose (11451 g) and carmellose calcium (540 g) were uniformly mixed in a fluid bed granulator (FD-S2, POWREX CORPORATION), and the mixture was granulated while spraying a binding solution (I), and dried to give a granule containing pioglitazone. A part of the obtained granule (3 batches) was pulverized with a screening mill (P-3, Showa Chemical Machinery) and a 1.5 mmϕ punching screen to give a milled granule. To a part (46980 g) of the obtained milled granule were added carmellose calcium (1458 g) and magnesium stearate (162 g), and they were mixed in a tumbler mixer (TM20-0-0, Suchiro Kakouki) to give granules. The obtained granules were tableted by a rotary tableting machine (Correct 19K, Kikusui Seisakusho) using a 7.5 mmϕ punch at a weight of 180 mg to give plain tablet containing pioglitazone (45 mg) per one tablet.
(2) Hydroxypropylmethylcellulose (TC-5 EW, Shin-Etsu Chemical Co., Ltd.; 45 g) and macrogol 6000 (5 g) were dissolved in purified water (450 g) to give coating solution (I). The coating solution (I) was sprayed in a coating machine (HC-LABO, Freund Corporation) on the plain tablet obtained in (1) until the weight of the plain tablet increased by 10 mg per one tablet to give coated tablet (I).
(3) Compound (IA) (272 g), hydroxypropylcellulose (grade SL-T, Nippon Soda Co., Ltd.; 24 g) and mannitol (104 g) were dissolved or suspended in purified water (2000 g) to give coating solution (II). The coating solution (II) was sprayed in a coating machine (HC-LABO, Freund Corporation) on the coated tablet (I) obtained in (2) until the weight of the coated tablet increased by 100 mg per one tablet to give coated tablet (B) containing compound (I) (50 mg) and pioglitazone (45 mg) per one tablet.

TABLE 3

| | component | formulation amount |
|---|---|---|
| plain tablet containing pioglitazone | pioglitazone hydrochloride | 49.59 mg |
| | lactose | 114.51 mg |
| | hydroxypropylcellulose | 4.5 mg |
| | carmellose calcium | 10.8 mg |
| | magnesium stearate | 0.6 mg |

TABLE 3-continued

| | component | formulation amount |
|---|---|---|
| intermediate layer | hydroxypropylmethylcellulose | 9 mg |
| | macrogol 6000 | 1 mg |
| layer containing compound (I) | compound (IA) | 68 mg |
| | mannitol | 26 mg |
| | hydroxypropylcellulose | 6 mg |

Example 4

According to the formulation shown in Table 4, the coated tablet (A) of the present invention was produced.
(1) Hydroxypropylcellulose (grade L, Nippon Soda Co., Ltd.; 2460 g) was dissolved in purified water (38540 g) to give a binding solution (I). Compound (IA) (3740 g), mannitol (54340 g) and microcrystalline cellulose (3850 g) were uniformly mixed in a fluid bed granulator (WSG-60, POWREX CORPORATION), and the mixture was granulated while spraying a binding solution (I) (33000 g) and dried to give a granule. A part of the obtained granule was pulverized with a screening mill (P-7S, Showa Chemical Machinery) and a 1.5 mmϕ punching screen to give a milled granule. To a part (60130 g) of the obtained milled granule were added microcrystalline cellulose (7245 g), croscarmellose sodium (4347 g) and magnesium stearate (724.5 g), and they were mixed in a tumbler mixer (TM-400S, Showa Chemical Machinery) to give granules. The obtained granules were tableted by a rotary tableting machine (AQUARIUS 0836SS2JII, Kikusui Seisakusho) using a 9.5 mmϕ punch at a weight of 350 mg to give plain tablet containing compound (I) (12.5 mg) per one tablet.
(2) Hydroxypropylmethylcellulose (TC-5 EW, Shin-Etsu Chemical Co., Ltd.; 5771 g) and talc (641.3 g) were dissolved or suspended in purified water (36340 g) to give coating solution (I). The coating solution (I) was sprayed in a coating machine (DRC-1200DS, POWREX CORPORATION) on the plain tablet obtained in (1) until the weight of the plain tablet increased by 15 mg per one tablet to give coated tablet (I).
(3) Pioglitazone hydrochloride (2069 g), hydroxypropylcellulose (grade SL-T, Nippon Soda Co., Ltd.; 375.5 g) and mannitol (15580 g) were dissolved or suspended in purified water (106400 g) to give coating solution (II). The coating solution (II) was sprayed in a coating machine (DRC-1200DS, POWREX CORPORATION) on the coated tablet (1) obtained in (2) until the weight of the coated tablet increased by 150 mg per one tablet to give coated tablet (II).
(4) Hydroxypropylmethylcellulose (HPMC) (TC-5 EW, Shin-Etsu Chemical Co., Ltd.; 5131 g) and macrogol 6000 (1026 g) were dissolved in purified water (29640 g) to give HPMC solution (I). Titanium dioxide (663.5 g) and yellow ferric oxide (20.52 g) were dispersed in purified water (9120 g) to give dispersion (I). Dispersion (I) was added to HPMC solution (I), and they were mixed by stirring in a stirrer (MXD-2302, Satake Chemical Equipment Mfg Ltd.) to give coating solution (III). The coating solution (III) was sprayed in a coating machine (DRC-1200DS, POWREX CORPORATION) on the coated tablet (II) obtained in (3) until the weight of the coated tablet increased by 15 mg per one tablet to give coated tablet (III).
(5) Macrogol 6000 (1848 g) was dissolved in purified water (16630 g) to give coating solution (IV). The coating solution (IV) was sprayed in a coating machine (DRC-1200DS, POWREX CORPORATION) on the coated tablet (III) obtained in (4) until the weight of the coated tablet increased by 0.25 mg per one tablet to give coated tablet (A) containing compound (I) (12.5 mg) and pioglitazone (15 mg) per one tablet.

TABLE 4

| | component | formulation amount |
|---|---|---|
| plain tablet containing compound (I) | compound (IA) | 17 mg |
| | mannitol | 247 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 16.53 mg |
| | mannitol | 130.47 mg |
| | hydroxypropylcellulose | 3 mg |
| film coating | hydroxypropylmethylcellulose | 11.25 mg |
| | macrogol 6000 | 2.25 mg |
| | titanium dioxide | 1.455 mg |
| | yellow ferric oxide | 0.045 mg |
| | macrogol 6000 | 0.25 mg |

Example 5

According to the formulation shown in Table 5, the coated tablet (A) of the present invention was produced.
(1) Hydroxypropylcellulose (grade L, Nippon Soda Co., Ltd.; 2460 g) was dissolved in purified water (38540 g) to give a binding solution (I). Compound (IA) (3740 g), mannitol (54340 g) and microcrystalline cellulose (3850 g) were uniformly mixed in a fluid bed granulator (WSG-60, POWREX CORPORATION), and the mixture was granulated while spraying a binding solution (I) (33000 g) and dried to give a granule. A part of the obtained granule was pulverized with a screening mill (P-7S, Showa Chemical Machinery) and a 1.5 mmϕ punching screen to give a milled granule. To a part (60130 g) of the obtained milled granule were added microcrystalline cellulose (7245 g), croscarmellose sodium (4347 g) and magnesium stearate (724.5 g), and they were mixed in a tumbler mixer (TM-400S, Showa Chemical Machinery) to give granules. The obtained granules were tableted by a rotary tableting machine (AQUARIUS 0836SS2JII, Kikusui Seisakusho) using a 9.5 mmϕ punch at a weight of 350 mg to give plain tablet containing compound (I) (12.5 mg) per one tablet.
(2) Hydroxypropylmethylcellulose (TC-5 EW, Shin-Etsu Chemical Co., Ltd.; 5771 g) and talc (641.3 g) were dissolved or suspended in purified water (36340 g) to give coating solution (I). The coating solution (I) was sprayed in a coating machine (DRC-1200DS, POWREX CORPORATION) on the plain tablet obtained in (1) until the weight of the plain tablet increased by 15 mg per one tablet to give coated tablet (I).
(3) Pioglitazone hydrochloride (4139 g), hydroxypropylcellulose (grade SL-T, Nippon Soda Co., Ltd.; 375.5 g) and mannitol (13510 g) were dissolved or suspended in purified water (106400 g) to give coating solution (II). The coating solution (II) was sprayed in a coating machine (DRC-1200DS, POWREX CORPORATION) on the coated tablet (1) obtained in (2) until the weight of the coated tablet increased by 150 mg per one tablet to give coated tablet (II).
(4) Hydroxypropylmethylcellulose (HPMC) (TC-5 EW, Shin-Etsu Chemical Co., Ltd.; 5131 g) and macrogol 6000 (1026 g) were dissolved in purified water (29640 g) to give HPMC solution (I). Titanium dioxide (663.5 g), yellow ferric oxide (14.36 g) and red ferric oxide (6.156 g) were dispersed in purified water (9120 g) to give dispersion (I). Dispersion (I)

was added to the HPMC solution (I), and they were mixed by stirring in a stirrer (MXD-2302, Satake Chemical Equipment Mfg Ltd.) to give coating solution (III). The coating solution (III) was sprayed in a coating machine (DRC-1200DS, POWREX CORPORATION) on the coated tablet (II) obtained in (3) until the weight of the coated tablet increased by 15 mg per one tablet to give coated tablet (III).

(5) Macrogol 6000 (1848 g) was dissolved in purified water (16630 g) to give coating solution (IV). The coating solution (IV) was sprayed in a coating machine (DRC-1200DS, POWREX CORPORATION) on the coated tablet (III) obtained in (4) until the weight of the coated tablet increased by 0.25 mg per one tablet to give coated tablet (A) containing compound (I) (12.5 mg) and pioglitazone (30 mg) per one tablet.

TABLE 5

| component | | formulation amount |
|---|---|---|
| plain tablet containing compound (I) | compound (IA) | 17 mg |
| | mannitol | 247 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 33.06 mg |
| | mannitol | 113.94 mg |
| | hydroxypropylcellulose | 3 mg |
| film coating | hydroxypropylmethylcellulose | 11.25 mg |
| | macrogol 6000 | 2.25 mg |
| | titanium dioxide | 1.455 mg |
| | yellow ferric oxide | 0.0315 mg |
| | red ferric oxide | 0.0135 mg |
| | macrogol 6000 | 0.25 mg |

Example 6

According to the formulation shown in Table 6, and by a method similar to that in Example 4, coated tablet (A) containing compound (I) (12.5 mg) and pioglitazone (45 mg) per one tablet was obtained.

TABLE 6

| component | | formulation amount |
|---|---|---|
| plain tablet containing compound (I) | compound (IA) | 17 mg |
| | mannitol | 247 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 49.59 mg |
| | mannitol | 97.41 mg |
| | hydroxypropylcellulose | 3 mg |
| film coating | hydroxypropylmethylcellulose | 11.25 mg |
| | macrogol 6000 | 2.25 mg |
| | titanium dioxide | 1.35 mg |
| | red ferric oxide | 0.15 mg |
| | macrogol 6000 | 0.25 mg |

Example 7

According to the formulation shown in Table 7, and by a method similar to that in Example 4, coated tablet (A) containing compound (I) (25 mg) and pioglitazone (15 mg) per one tablet was obtained.

TABLE 7

| component | | formulation amount |
|---|---|---|
| plain tablet containing compound (I) | compound (IA) | 34 mg |
| | mannitol | 230 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 16.53 mg |
| | mannitol | 130.47 mg |
| | hydroxypropylcellulose | 3 mg |
| film coating | hydroxypropylmethylcellulose | 11.25 mg |
| | macrogol 6000 | 2.25 mg |
| | titanium dioxide | 1.35 mg |
| | yellow ferric oxide | 0.15 mg |
| | macrogol 6000 | 0.25 mg |

Example 8

According to the formulation shown in Table 8, the coated tablet (A) of the present invention was produced.

(1) Hydroxypropylcellulose (grade L, Nippon Soda Co., Ltd.; 2460 g) was dissolved in purified water (38540 g) to give a binding solution (I). Compound (IA) (7480 g), mannitol (50600 g) and microcrystalline cellulose (3850 g) were uniformly mixed in a fluid bed granulator (WSG-60, POWREX CORPORATION), and the mixture was granulated while spraying a binding solution (I) (33000 g) and dried to give a granule. A part of the obtained granule was pulverized with a screening mill (P-7S, Showa Chemical Machinery) and a 1.5 mmϕ punching screen to give a milled granule. To a part (60130 g) of the obtained milled granule were added microcrystalline cellulose (7245 g), croscarmellose sodium (4347 g) and magnesium stearate (724.5 g), and they were mixed in a tumbler mixer (TM-400S, Showa Chemical Machinery) to give granules. The obtained granules were tableted by a rotary tableting machine (AQUARIUS 0836SS2JII, Kikusui Seisakusho) using a 9.5 mmϕ punch at a weight of 350 mg to give a plain tablet containing compound (I) (25 mg) per one tablet.

(2) Hydroxypropylmethylcellulose (TC-5 EW, Shin-Etsu Chemical Co., Ltd.; 5771 g) and talc (641.3 g) were dissolved or suspended in purified water (36340 g) to give coating solution (I). The coating solution (I) was sprayed in a coating machine (DRC-1200DS, POWREX CORPORATION) on the plain tablet obtained in (1) until the weight of the plain tablet increased by 15 mg per one tablet to give coated tablet (I).

(3) Pioglitazone hydrochloride (4139 g), hydroxypropylcellulose (grade SL-T, Nippon Soda Co., Ltd.; 375.5 g) and mannitol (13510 g) were dissolved or suspended in purified water (106400 g) to give coating solution (II). The coating solution (II) was sprayed in a coating machine (DRC-1200DS, POWREX CORPORATION) on the coated tablet (1) obtained in (2) until the weight of the coated tablet increased by 150 mg per one tablet to give coated tablet (II).

(4) Hydroxypropylmethylcellulose (HPMC) (TC-5 EW, Shin-Etsu Chemical Co., Ltd.; 5131 g) and macrogol 6000 (1026 g) were dissolved in purified water (29640 g) to give HPMC solution (I). Titanium dioxide (615.6 g), yellow ferric oxide (47.88 g) and red ferric oxide (20.52 g) were dispersed in purified water (9120 g) to give dispersion (I). Dispersion (I) was added to the HPMC solution (I), and they were mixed by stirring in a stirrer (MXD-2302, Satake Chemical Equipment Mfg Ltd.) to give coating solution (III). The coating solution (III) was sprayed in a coating machine (DRC-1200DS, POWREX CORPORATION) on the coated tablet (II) obtained in (3) until the weight of the coated tablet increased by 15 mg per one tablet to give coated tablet (III).

(5) Macrogol 6000 (1848 g) was dissolved in purified water (16630 g) to give coating solution (IV). The coating solution (IV) was sprayed in a coating machine (DRC-1200DS, POWREX CORPORATION) on the coated tablet (III) obtained in (4) until the weight of the coated tablet increased by 0.25 mg per one tablet to give coated tablet (A) containing compound (I) (25 mg) and pioglitazone (30 mg) per one tablet.

TABLE 8

| | component | formulation amount |
|---|---|---|
| plain tablet containing compound (I) | compound (IA) | 34 mg |
| | mannitol | 230 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 33.06 mg |
| | mannitol | 113.94 mg |
| | hydroxypropylcellulose | 3 mg |
| film coating | hydroxypropylmethylcellulose | 11.25 mg |
| | macrogol 6000 | 2.25 mg |
| | titanium dioxide | 1.35 mg |
| | yellow ferric oxide | 0.105 mg |
| | red ferric oxide | 0.045 mg |
| | macrogol 6000 | 0.25 mg |

Example 9

According to the formulation shown in Table 9, and by a method similar to that in Example 4, coated tablet (A) containing compound (I) (25 mg) and pioglitazone (45 mg) per one tablet was obtained.

TABLE 9

| | component | formulation amount |
|---|---|---|
| plain tablet containing compound (I) | compound (IA) | 34 mg |
| | mannitol | 230 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 49.59 mg |
| | mannitol | 97.41 mg |
| | hydroxypropylcellulose | 3 mg |
| film coating | hydroxypropylmethylcellulose | 11.25 mg |
| | macrogol 6000 | 2.25 mg |
| | titanium dioxide | 1.05 mg |
| | red ferric oxide | 0.45 mg |
| | macrogol 6000 | 0.25 mg |

Example 10

According to the formulation shown in Table 10, multi-layer tablet (A) of the present invention was produced.
(1) Hydroxypropylcellulose (grade L, Nippon Soda Co., Ltd.; 2250 g) was dissolved in purified water (35250 g) to give a binding solution (I). Compound (IA) (benzoate of compound (I); 13260 g), mannitol (45630 g) and microcrystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added microcrystalline cellulose (7250 g), croscarmellose sodium (4350 g) and magnesium stearate (725 g), and the mixture was mixed in a tumbler mixer (TM-400S, Showa Chemical Machinery) to give granule (1).

(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (6777 g), lactose (44070 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-400S, Showa Chemical Machinery) to give granule (II).

(3) Granule (I) (100 mg) and granule (II) (180 mg) were formed into a multi-layer by a rotary tableting machine (AQUA 08242L2JI, Kikusui Seisakusho) using a 8.5 mmφ punch to give a plain tablet.

(4) Hydroxypropylmethylcellulose (TC-5 RW, Shin-Etsu Chemical Co., Ltd.; 1365 g) and talc (210 g) were dispersed in purified water (12250 g) to give dispersion (I). Titanium dioxide (169.8 g) and yellow ferric oxide (5.25 g) were dispersed in purified water (2625 g) to give dispersion (II). Dispersion (II) and purified water (875 g) were added to dispersion (I), and they were mixed by stirring in a stirrer (LR400D, Yamato Scientific Co., Ltd.) to give coating solution (I). The coating solution (I) was sprayed in a coating machine (HCF(S)-100N, Freund Corporation) on the plain tablet obtained in (3) until the weight of the plain tablet increased by 10 mg per one tablet to give multi-layer tablet (I).

(5) Macrogol 6000 (90 g) was dissolved in purified water (1710 g) to give coating solution (II). The coating solution (II) was sprayed in a coating machine (HCF(S)-100N, Freund Corporation) on the multi-layer tablet (I) obtained in (4) until the weight of the multi-layer tablet increased by 0.15 mg per one tablet to give multi-layer tablet (A) containing compound (I) (12.5 mg) and pioglitazone (15 mg) per one tablet.

TABLE 10

| | component | formulation amount |
|---|---|---|
| layer containing compound (I) | compound (IA) | 17 mg |
| | mannitol | 58.5 mg |
| | microcrystalline cellulose | 15 mg |
| | hydroxypropylcellulose | 2.5 mg |
| | croscarmellose sodium | 6 mg |
| | magnesium stearate | 1 mg |

TABLE 10-continued

| component | | formulation amount |
|---|---|---|
| layer containing pioglitazone | pioglitazone hydrochloride | 16.53 mg |
| | lactose | 143.49 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.97 mg |
| | yellow ferric oxide | 0.03 mg |
| | macrogol 6000 | 0.15 mg |

Example 11

According to the formulation shown in Table 11, multi-layer tablet (A) of the present invention was produced.
(1) Hydroxypropylcellulose (grade L, Nippon Soda Co., Ltd.; 2250 g) was dissolved in purified water (35250 g) to give a binding solution (I). Compound (IA) (benzoate of compound (I); 13260 g), mannitol (45630 g) and microcrystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added microcrystalline cellulose (7250 g), croscarmellose sodium (4350 g) and magnesium stearate (725 g), and the mixture was mixed in a tumbler mixer (TM-400S, Showa Chemical Machinery) to give granule (1).
(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (13550 g), lactose (37290 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-400S, Showa Chemical Machinery) to give granule (II).
(3) Granule (I) (100 mg) and granule (II) (180 mg) were formed into a multi-layer by a rotary tableting machine (AQUA 08242L2JI, Kikusui Seisakusho) using a 8.5 mmφ punch to give a plain tablet.
(4) Hydroxypropylmethylcellulose (TC-5 RW, Shin-Etsu Chemical Co., Ltd.; 1365 g) and talc (210 g) were dispersed in purified water (12250 g) to give dispersion (I). Titanium dioxide (169.8 g), yellow ferric oxide (3.675 g) and red ferric oxide (1.575 g) were dispersed in purified water (2625 g) to give dispersion (II). Dispersion (II) and purified water (875 g) were added to dispersion (I), and they were mixed by stirring in a stirrer (LR400D, Yamato Scientific Co., Ltd.) to give coating solution (I). The coating solution (I) was sprayed in a coating machine (HCF(S)-100N, Freund Corporation) on the plain tablet obtained in (3) until the weight of the plain tablet increased by 10 mg per one tablet to give multi-layer tablet (I).
(5) Macrogol 6000 (90 g) was dissolved in purified water (1710 g) to give coating solution (II). The coating solution (II) was sprayed in a coating machine (HCF(S)-100N, Freund Corporation) on the multi-layer tablet (I) obtained in (4) is until the weight of the multi-layer tablet increased by 0.15 mg per one tablet to give multi-layer tablet (A) containing compound (I) (12.5 mg) and pioglitazone (30 mg) per one tablet.

TABLE 11

| component | | formulation amount |
|---|---|---|
| layer containing compound (I) | compound (IA) | 17 mg |
| | mannitol | 58.5 mg |
| | microcrystalline cellulose | 15 mg |
| | hydroxypropylcellulose | 2.5 mg |
| | croscarmellose sodium | 6 mg |
| | magnesium stearate | 1 mg |
| layer containing pioglitazone | pioglitazone hydrochloride | 33.06 mg |
| | lactose | 126.96 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.97 mg |
| | yellow ferric oxide | 0.021 mg |
| | red ferric oxide | 0.009 mg |
| | macrogol 6000 | 0.15 mg |

Example 12

According to the formulation shown in Table 12, multi-layer tablet (A) of the present invention was produced.
(1) Hydroxypropylcellulose (grade L, Nippon Soda Co., Ltd.; 2250 g) was dissolved in purified water (35250 g) to give a binding solution (I). Compound (IA) (benzoate of compound (I); 13260 g), mannitol (45630 g) and microcrystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added microcrystalline cellulose (7250 g), croscarmellose sodium (4350 g) and magnesium stearate (725 g), and the mixture was mixed in a tumbler mixer (TM-400S, Showa Chemical Machinery) to give granule (1).
(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (20330 g), lactose (30520 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-4005, Showa Chemical Machinery) to give granule (II).

(3) Granule (I) (100 mg) and granule (II) (180 mg) were formed into a multi-layer by a rotary tableting machine (AQUA 08242L2JI, Kikusui Seisakusho) using a 8.5 mmφ punch to give a plain tablet.

Hydroxypropylmethylcellulose (TC-5 RW, Shin-Etsu Chemical Co., Ltd.; 1365 g) and talc (210 g) were dispersed in purified water (12250 g) to give dispersion (I). Titanium dioxide (157.5 g) and red ferric oxide (17.50 g) were dispersed in purified water (2625 g) to give dispersion (II). Dispersion (II) and purified water (875 g) were added to dispersion (I), and they were mixed by stirring in a stirrer (LR400D, Yamato Scientific Co., Ltd.) to give coating solution (I). The coating solution (I) was sprayed in a coating machine (HCF(S)-100N, Freund Corporation) on the plain tablet obtained in (3) until the weight of the plain tablet increased by 10 mg per one tablet to give multi-layer tablet (I).

(5) Macrogol 6000 (90 g) was dissolved in purified water (1710 g) to give coating solution (II). The coating solution (II) was sprayed in a coating machine (HCF(S)-100N, Freund Corporation) on the multi-layer tablet (I) obtained in (4) until the weight of the multi-layer tablet increased by 0.15 mg per one tablet to give multi-layer tablet (A) containing compound (I) (12.5 mg) and pioglitazone (45 mg) per one tablet.

TABLE 12

| | component | formulation amount |
|---|---|---|
| layer containing compound (I) | compound (IA) | 17 mg |
| | mannitol | 58.5 mg |
| | microcrystalline cellulose | 15 mg |
| | hydroxypropylcellulose | 2.5 mg |
| | croscarmellose sodium | 6 mg |
| | magnesium stearate | 1 mg |
| layer containing pioglitazone | pioglitazone hydrochloride | 49.59 mg |
| | lactose | 110.43 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.9 mg |
| | red ferric oxide | 0.1 mg |
| | macrogol 6000 | 0.15 mg |

Example 13

According to the formulation shown in Table 13, multi-layer tablet (A) of the present invention was produced.

(1) Hydroxypropylcellulose (grade L, Nippon Soda Co., Ltd.; 2250 g) was dissolved in purified water (35250 g) to give a binding solution (I). Compound (IA) (benzoate of compound (I); 26520 g), mannitol (32370 g) and microcrystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added microcrystalline cellulose (7250 g), croscarmellose sodium (4350 g) and magnesium stearate (725 g), and the mixture was mixed in a tumbler mixer (TM-400S, Showa Chemical Machinery) to give granule (1).

(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (6777 g), lactose (44070 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-400S, Showa Chemical Machinery) to give granule (II).

(3) Granule (I) (100 mg) and granule (II) (180 mg) were formed into a multi-layer by a rotary tableting machine (AQUA 08242L2JI, Kikusui Seisakusho) using a 8.5 mmφ punch to give a plain tablet.

(4) Hydroxypropylmethylcellulose (TC-5 RW, Shin-Etsu Chemical Co., Ltd.; 1365 g) and talc (210 g) were dispersed in purified water (12250 g) to give dispersion (I). Titanium dioxide (157.5 g) and yellow ferric oxide (17.5 g) were dispersed in purified water (2625 g) to give dispersion (II). Dispersion (II) and purified water (875 g) were added to dispersion (I), and they were mixed by stirring in a stirrer (LR400D, Yamato Scientific Co., Ltd.) to give coating solution (I). The coating solution (I) was sprayed in a coating machine (HCF(S)-100N, Freund Corporation) on the plain tablet obtained in (3) until the weight of the plain tablet increased by 10 mg per one tablet to give multi-layer tablet (I).

(5) Macrogol 6000 (90 g) was dissolved in purified water (1710 g) to give coating solution (II). The coating solution (II) was sprayed in a coating machine (HCF(S)-100N, Freund Corporation) on the multi-layer tablet (I) obtained in (4) until the weight of the multi-layer tablet increased by 0.15 mg per one tablet to give multi-layer tablet (A) containing compound (I) (25 mg) and pioglitazone (15 mg) per one tablet.

TABLE 13

| | component | formulation amount |
|---|---|---|
| layer containing compound (I) | compound (IA) | 34 mg |
| | mannitol | 41.5 mg |
| | microcrystalline cellulose | 15 mg |
| | hydroxypropylcellulose | 2.5 mg |
| | croscarmellose sodium | 6 mg |
| | magnesium stearate | 1 mg |
| layer containing pioglitazone | pioglitazone hydrochloride | 16.53 mg |
| | lactose | 143.49 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.9 mg |
| | yellow ferric oxide | 0.1 mg |
| | macrogol 6000 | 0.15 mg |

Example 14

According to the formulation shown in Table 14, multi-layer tablet (A) of the present invention was produced.

(1) Hydroxypropylcellulose (grade L, Nippon Soda Co., Ltd.; 2250 g) was dissolved in purified water (35250 g) to give a binding solution (I). Compound (IA) (benzoate of compound (I); 26520 g), mannitol (32370 g) and microcrystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added microcrystalline cellulose (7250 g), croscarmellose sodium (4350 g) and magnesium stearate (725 g), and the mixture was mixed in a tumbler mixer (TM-400S, Showa Chemical Machinery) to give granule (1).

(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (13550 g), lactose (37290 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained is granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-400S, Showa Chemical Machinery) to give granule (II).

(3) Granule (I) (100 mg) and granule (II) (180 mg) were formed into a multi-layer by a rotary tableting machine (AQUA 08242L2JI, Kikusui Seisakusho) using a 8.5 mmφ punch to give a plain tablet.

(4) Hydroxypropylmethylcellulose (TC-5 RW, Shin-Etsu Chemical Co., Ltd.; 1365 g) and talc (210 g) were dispersed in purified water (12250 g) to give dispersion (I). Titanium dioxide (157.5 g), yellow ferric oxide (12.25 g) and red ferric oxide (5.25 g) were dispersed in purified water (2625 g) to give dispersion (II). Dispersion (II) and purified water (875 g) were added to dispersion (I), and they were mixed by stirring in a stirrer (LR400D, Yamato Scientific Co., Ltd.) to give coating solution (I). The coating solution (I) was sprayed in a coating machine (HCF(S)-100N, Freund Corporation) on the plain tablet obtained in (3) until the weight of the plain tablet increased by 10 mg per one tablet to give multi-layer tablet (I).

(5) Macrogol 6000 (90 g) was dissolved in purified water (1710 g) to give coating solution (II). The coating solution (II) was sprayed in a coating machine (HCF(S)-100N, Freund Corporation) on the multi-layer tablet (I) obtained in (4) until the weight of the multi-layer tablet increased by 0.15 mg per one tablet to give multi-layer tablet (A) containing compound (I) (25 mg) and pioglitazone (30 mg) per one tablet.

TABLE 14

| | component | formulation amount |
|---|---|---|
| layer containing compound (I) | compound (IA) | 34 mg |
| | mannitol | 41.5 mg |
| | microcrystalline cellulose | 15 mg |
| | hydroxypropylcellulose | 2.5 mg |
| | croscarmellose sodium | 6 mg |
| | magnesium stearate | 1 mg |
| layer containing pioglitazone | pioglitazone hydrochloride | 33.06 mg |
| | lactose | 126.96 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.9 mg |
| | yellow ferric oxide | 0.07 mg |
| | red ferric oxide | 0.03 mg |
| | macrogol 6000 | 0.15 mg |

Example 15

According to the formulation shown in Table 15, multi-layer tablet (A) of the present invention was produced.

(1) Hydroxypropylcellulose (grade L, Nippon Soda Co., Ltd.; 2250 g) was dissolved in purified water (35250 g) to give a binding solution (I). Compound (IA) (benzoate of compound (I); 26520 g), mannitol (32370 g) and crystalline cellulose (3900 g) were uniformly mixed in a fluid bed granulator (WSG-60, POWREX CORPORATION), and the mixture was granulated while spraying a binding solution (I) (32500 g) and dried to give a granule. A part of the obtained granule was pulverized with a screening mill (P-7S, Showa Chemical Machinery) and a 1.5 mmφ punching screen to give a milled granule. To a part (60180 g) of the obtained milled granule were added crystalline cellulose (7250 g), croscarmellose sodium (4350 g) and magnesium stearate (725 g), and the mixture was mixed in a tumbler mixer (TM-400S, Showa Chemical Machinery) to give granule (1).

(2) Hydroxypropylcellulose (grade L, Nippon Soda Co., Ltd.; 1802 g) was dissolved in purified water (34290 g) to give a binding solution (II). Hydroxypropylcellulose (grade L, Nippon Soda Co., Ltd.; 1976 g) was dissolved in purified water (73320 g), and lactose (18720 g) was dispersed therein to give suspension (I). Pioglitazone hydrochloride (20330 g), lactose (30520 g) and croscarmellose sodium (2706 g) were uniformly mixed in a fluid bed granulator (WSG-60, POWREX CORPORATION), and the mixture was granulated while spraying a binding solution (II) (27920 g), sprayed with suspension (I) (74130 g), and then dried to give a granule. A part of the obtained granule was pulverized with a screening mill (P-7S, Showa Chemical Machinery) and a 1.5 mmφ punching screen to give a milled granule. To a part (66050 g) of the obtained milled granule were added croscarmellose sodium (2075 g) and magnesium stearate (273.6 g), and they were mixed in a tumbler mixer (TM-400S, Showa Chemical Machinery) to give granule (II).

(3) Granule (I) (100 mg) and granule (II) (180 mg) were formed into a multi-layer by a rotary tableting machine (AQUA 08242L2JI, Kikusui Seisakusho) using a 8.5 mmφ punch to give a plain tablet.

(4) Hydroxypropylmethylcellulose (TC-5 RW, Shin-Etsu Chemical Co., Ltd.; 1365 g) and talc (210 g) were dispersed in purified water (12250 g) to give dispersion (I). Titanium dioxide (122.5 g) and red ferric oxide (52.5 g) were dispersed in purified water (2625 g) to give dispersion (II). Dispersion (II) and purified water (875 g) were added to dispersion (I), and they were mixed by stirring in a stirrer (LR400D, Yamato Scientific Co., Ltd.) to give coating solution (I). The coating solution (I) was sprayed in a coating machine (HCF(S)-100N, Freund Corporation) on the plain tablet obtained in (3) until the weight of the plain tablet increased by 10 mg per one tablet to give multi-layer tablet (I).
(5) Macrogol 6000 (90 g) was dissolved in purified water (1710 g) to give coating solution (II). The coating solution (II) was sprayed in a coating machine (HCF(S)-100N, Freund Corporation) on the multi-layer tablet (I) obtained in (4) until the weight of the multi-layer tablet increased by 0.15 mg per one tablet to give multi-layer tablet (A) containing compound (I) (25 mg) and pioglitazone (45 mg) per one tablet.

TABLE 15

| | component | formulation amount |
|---|---|---|
| layer containing compound (I) | compound (IA) | 34 mg |
| | mannitol | 41.5 mg |
| | microcrystalline cellulose | 15 mg |
| | hydroxypropylcellulose | 2.5 mg |
| | croscarmellose sodium | 6 mg |
| | magnesium stearate | 1 mg |
| layer containing pioglitazone | pioglitazone hydrochloride | 49.59 mg |
| | lactose | 110.43 mg |
| | hydroxypropylcellulose | 7.2 mg |
| | croscarmellose sodium | 12.06 mg |
| | magnesium stearate | 0.72 mg |
| film coating | hydroxypropylmethylcellulose | 7.8 mg |
| | talc | 1.2 mg |
| | titanium dioxide | 0.7 mg |
| | red ferric oxide | 0.3 mg |
| | macrogol 6000 | 0.15 mg |

Example 16

According to the formulation shown in Table 16, the coated tablet (A) of the present invention was produced.
(1) Hydroxypropylcellulose (grade L, Nippon Soda Co., Ltd.; 2460 g) was dissolved in purified water (38540 g) to give a binding solution (I). Compound (IA) (3740 g), mannitol (54340 g) and microcrystalline cellulose (3850 g) were uniformly mixed in a fluid bed granulator (WSG-60, POWREX CORPORATION), and the mixture was granulated while spraying a binding solution (I) (33000 g) and dried to give a granule. A part of the obtained granule was pulverized with a screening mill (P-7S, Showa Chemical Machinery) and a 1.5 mmϕ punching screen to give a milled granule. To a part (60130 g) of the obtained milled granule were added microcrystalline cellulose (7245 g), croscarmellose sodium (4347 g) and magnesium stearate (724.5 g), and they were mixed in a tumbler mixer (TM-400S, Showa Chemical Machinery) to give granules. The obtained granules were tableted by a rotary tableting machine (AQUARIUS 0836SS2JII, Kikusui Seisakusho) using a 9.5 mmϕ punch at a weight of 350 mg to give plain tablet containing compound (I) (12.5 mg) per one tablet.
(2) Hydroxypropylmethylcellulose (TC-5 EW, Shin-Etsu Chemical Co., Ltd.; 5805 g) and talc (645.0 g) were dissolved or suspended in purified water (36550 g) to give coating solution (I). The coating solution (I) was sprayed in a coating machine (DRC-1200DS, POWREX CORPORATION) on the plain tablet obtained in (1) until the weight of the plain tablet increased by 15 mg per one tablet to give coated tablet (I).
(3) Pioglitazone hydrochloride (5290 g), hydroxypropylcellulose (grade SL-T, Nippon Soda Co., Ltd.; 480.0 g) and mannitol (17270 g) were dissolved or suspended in purified water (136000 g) to give coating solution (II). The coating solution (II) was sprayed in a coating machine (DRC-1200DS, POWREX CORPORATION) on the coated tablet (1) obtained in (2) until the weight of the coated tablet increased by 75 mg per one tablet to give coated tablet (II).
(4) Hydroxypropylmethylcellulose (HPMC) (TC-5 EW, Shin-Etsu Chemical Co., Ltd.; 5760 g) and macrogol 6000 (1152 g) were dissolved in purified water (35200 g) to give HPMC solution (I). Titanium dioxide (745.0 g) and yellow ferric oxide (23.04 g) were dispersed in purified water (8320 g) to give dispersion (I). Dispersion (I) was added to the HPMC solution (I), and they were mixed by stirring in a stirrer (MXD-2302, Satake Chemical Equipment Mfg Ltd.) to give coating solution (III). The coating solution (III) was sprayed in a coating machine (DRC-1200DS, POWREX CORPORATION) on the coated tablet (II) obtained in (3) until the weight of the coated tablet increased by 12 mg per one tablet to give coated tablet (A) containing compound (I) (12.5 mg) and pioglitazone (15 mg) per one tablet.

TABLE 16

| | component | formulation amount |
|---|---|---|
| plain tablet containing compound (I) | compound (IA) | 17 mg |
| | mannitol | 247 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 16.53 mg |
| | mannitol | 56.97 mg |
| | hydroxypropylcellulose | 1.5 mg |
| film coating | hydroxypropylmethylcellulose | 9 mg |
| | macrogol 6000 | 1.8 mg |
| | titanium dioxide | 1.164 mg |
| | yellow ferric oxide | 0.036 mg |

Example 17

Using a method similar to that of Example 16, and according to the formulation of Table 17, coated tablet (A) containing compound (I) (25 mg) and pioglitazone (15 mg) per one tablet can be obtained.

TABLE 17

| | component | formulation amount |
|---|---|---|
| plain tablet containing compound (I) | compound (IA) | 34 mg |
| | mannitol | 230 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 16.53 mg |
| | mannitol | 56.97 mg |
| | hydroxypropylcellulose | 1.5 mg |
| film coating | hydroxypropylmethylcellulose | 9 mg |
| | macrogol 6000 | 1.8 mg |
| | titanium dioxide | 1.08 mg |
| | yellow ferric oxide | 0.12 mg |

Example 18

According to the formulation shown in Table 18, the coated tablet (A) of the present invention was produced.
(1) Hydroxypropylcellulose (grade L, Nippon Soda Co., Ltd.; 2460 g) was dissolved in purified water (38540 g) to give a binding solution (I). Compound (IA) (7480 g), mannitol (50600 g) and microcrystalline cellulose (3850 g) were uniformly mixed in a fluid bed granulator (WSG-60, POWREX CORPORATION), and the mixture was granulated while spraying a binding solution (I) (33000 g) and dried to give a granule. A part of the obtained granule was pulverized with a screening mill (P-7S, Showa Chemical Machinery) and a 1.5 mmϕ punching screen to give a milled granule. To a part (60130 g) of the obtained milled granule were added microcrystalline cellulose (7245 g), croscarmellose sodium (4347 g) and magnesium stearate (724.5 g), and they were mixed in a tumbler mixer (TM-400S, Showa Chemical Machinery) to give granules. The obtained granules were tableted by a rotary tableting machine (AQUARIUS 0836SS2JII, Kikusui Seisakusho) using a 9.5 mmϕ punch at a weight of 350 mg to give plain tablet containing compound (I) (25 mg) per one tablet.
(2) Hydroxypropylmethylcellulose (TC-5 EW, Shin-Etsu Chemical Co., Ltd.; 5805 g) and talc (645.0 g) were dissolved or suspended in purified water (36550 g) to give coating solution (I). The coating solution (I) was sprayed in a coating machine (DRC-1200DS, POWREX CORPORATION) on the plain tablet obtained in (1) until the weight of the plain tablet increased by 15 mg per one tablet to give coated tablet (I).
(3) Pioglitazone hydrochloride (12950 g), hydroxypropylcellulose (grade SL-T, Nippon Soda Co., Ltd.; 1175 g) and mannitol (42790 g) were dissolved or suspended in purified water (235000 g) to give coating solution (II). The coating solution (II) was sprayed in a coating machine (DRC-1200DS, POWREX CORPORATION) on the coated tablet (1) obtained in (2) until the weight of the coated tablet increased by 225 mg per one tablet to give coated tablet (II).
(4) Hydroxypropylmethylcellulose (HPMC) (TC-5 EW, Shin-Etsu Chemical Co., Ltd.; 5940 g) and macrogol 6000 (1188 g) were dissolved in purified water (36080 g) to give HPMC solution (I). Titanium dioxide (554.4 g) and red ferric oxide (237.6 g) were dispersed in purified water (8800 g) to give dispersion (I). Dispersion (I) was added to the HPMC solution (I), and they were mixed by stirring in a stirrer (MXD-2302, Satake Chemical Equipment Mfg Ltd.) to give coating solution (III). The coating solution (III) was sprayed in a coating machine (DRC-1200DS, POWREX CORPORATION) on the coated tablet (II) obtained in (3) until the weight of the coated tablet increased by 18 mg per one tablet to give coated tablet (A) containing compound (I) (25 mg) and pioglitazone (45 mg) per one tablet.

TABLE 18

| component | | formulation amount |
|---|---|---|
| plain tablet containing compound (I) | compound (IA) | 34 mg |
| | mannitol | 230 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 49.59 mg |
| | mannitol | 170.91 mg |
| | hydroxypropylcellulose | 4.5 mg |
| pioglitazone film coating | hydroxypropylmethylcellulose | 13.5 mg |
| | macrogol 6000 | 2.7 mg |
| | titanium dioxide | 1.26 mg |
| | red ferric oxide | 0.54 mg |

Example 19

Using a method similar to that of Example 18 and according to the formulation of Table 19, coated tablet (A) containing compound (I) (12.5 mg) and pioglitazone (45 mg) per one tablet can be obtained.

TABLE 19

| component | | formulation amount |
|---|---|---|
| plain tablet containing Compound (I) | compound (IA) | 17 mg |
| | mannitol | 247 mg |
| | microcrystalline cellulose | 52.5 mg |
| | hydroxypropylcellulose | 9 mg |
| | croscarmellose sodium | 21 mg |
| | magnesium stearate | 3.5 mg |
| intermediate layer | hydroxypropylmethylcellulose | 13.5 mg |
| | talc | 1.5 mg |
| layer containing pioglitazone | pioglitazone hydrochloride | 49.59 mg |
| | mannitol | 170.91 mg |
| | hydroxypropylcellulose | 4.5 mg |
| pioglitazone film coating | hydroxypropylmethylcellulose | 13.5 mg |
| | macrogol 6000 | 2.7 mg |
| | titanium dioxide | 1.62 mg |
| | red ferric oxide | 0.18 mg |

Comparative Example 1

Compound (IA) (50 mg) was weighed.

Comparative Example 2

Compound (IA) (800 mg) and pioglitazone hydrochloride (793.44 mg) were uniformly mixed with a pestle in a mortar to give a compound (IA)/pioglitazone hydrochloride (1:1) mixture.

Comparative Example 3

Compound (IA) (1200 mg) and lactose (6000 mg) were uniformly mixed with a pestle in a mortar to give a compound (IA)/lactose (1:5) mixture.

Comparative Example 4

According to the formulation shown in Table 20, a single layer tablet (A) containing compound (I) and pioglitazone was produced.
Hydroxypropylcellulose (grade L, Nippon Soda Co., Ltd.; 13.2 g) was dissolved in purified water (206.8 g) to give a binding solution (I). Compound (IA) (109.1 g), pioglitazone hydrochloride (149.6 g), lactose (169.4 g) and microcrystalline cellulose (52.8 g) were uniformly mixed in a fluid bed granulator (LAB-1, POWREX CORPORATION), and the mixture was granulated while spraying a binding solution (I) and dried to give a granule. A part of the obtained granule was pulverized with a screening mill (P-3, Showa Chemical Machinery) and a 1.5 mmϕ punching screen to give a milled granule. To a part (449.2 g) of the obtained milled granule were added croscarmellose sodium (28.8 g) and magnesium stearate (2 g), and they were mixed in a tumbler mixer (TM-15, Showa Chemical Machinery) to give granules. The obtained granules were tableted by a rotary tableting machine (Correct 19K, Kikusui Seisakusho) using a 8.5 mmφ punch at a weight of 240 mg to give single layer tablet (A) containing compound (I) (50 mg) and pioglitazone (45 mg) per one tablet.

TABLE 20

| component | formulation amount |
|---|---|
| compound (IA) | 68 mg |
| pioglitazone hydrochloride | 49.59 mg |
| lactose | 77.01 mg |
| microcrystalline cellulose | 24 mg |
| hydroxypropylcellulose | 6 mg |
| croscarmellose sodium | 14.4 mg |
| magnesium stearate | 1 mg |

Comparative Example 5

According to the formulation shown in Table 21 and by a method similar to that in Comparative Example 4 except that mannitol was used as an excipient, a single layer tablet (B) containing compound (I) (50 mg) and pioglitazone (45 mg) per one tablet was produced.

TABLE 21

| component | formulation amount |
|---|---|
| compound (IA) | 68 mg |
| pioglitazone hydrochloride | 49.59 mg |
| mannitol | 75.61 mg |
| microcrystalline cellulose | 24 mg |
| hydroxypropylcellulose | 6 mg |
| croscarmellose sodium | 14.4 mg |
| magnesium stearate | 2.4 mg |

Experimental Example 1

Compound (IA) (50 mg) of Comparative Example 1, the mixture (99.59 mg) of Comparative Example 2, and tablets of Example 1 and Example 2 were preserved in glass bottles at 40° C., 75% RH with opened cap or at 60° C. with closed cap and the amount of benzoic acid remaining as compound (IA) was measured to evaluate the chemical stability. The results are shown in Table 22.

TABLE 22

| | conditions | residual benzoic acid |
|---|---|---|
| Comparative Example 1 | Initial | 99.8% |
| | 40° C., 75% RH, opened bottle, 2 week storage product | 99.2% |
| | 60° C., closed bottle, 2 week storage product | 99.0% |
| Comparative Example 2 | Initial | 101.0% |
| | 40° C., 75% RH, opened bottle, 2 week storage product | 89.4% |
| | 60° C., closed bottle, 2 week storage product | 80.0% |

TABLE 22-continued

| | conditions | residual benzoic acid |
|---|---|---|
| Example 1 | Initial | 99.3% |
| | 40° C., 75% RH, 1 month storage product | 99.0% |
| | 60° C., closed bottle, 1 month storage product | 99.3% |
| Example 2 | Initial | 99.2% |
| | 40° C., 75% RH, 1 month storage product | 100.9% |
| | 60° C., closed bottle, 1 month storage product | 100.9% |

As shown in Table 22, it has been shown that the tablet of the present invention is superior in the chemical stability.

Experimental Example 2

The mixture (408 mg) of Comparative Example 3, and tablets of Comparative Example 4, Example 1 and Example 2 were each preserved in a glass bottle at 60° C. with closed cap, and the amount of all related substances derived from compound (I) (desmethyl form, dibenzyl form, dimer and the like of compound (I)) was measured. The results are shown in Table 23.

TABLE 23

| | conditions | all related substances derived from compound (I) |
|---|---|---|
| Comparative Example 3 | Initial | 0.15% |
| | 60° C., closed bottle, 2 week storage product | 0.58% |
| Comparative Example 4 | Initial | 0.16% |
| | 60° C., closed bottle, 2 week storage product | 1.15% |
| Example 1 | Initial | <0.04% |
| | 60° C., closed bottle, 1 month storage product | <0.04% |
| Example 2 | Initial | <0.04% |
| | 60° C., closed bottle, 1 month storage product | 0.20% |

As shown in Table 23, it has been shown that the tablet of the present invention is superior in the chemical stability.

Experimental Example 3

The dissolution property of pioglitazone hydrochloride in the tablets of Comparative Example 5, Example 1, Example 2 and Example 3 was evaluated by the Paddle Method (50 rpm) using 0.3 M hydrochloric acid-potassium chloride buffer (37° C., pH 2.0, 900 mL). The results are shown in Table 24. In the Table, each value shows an average value of the dissolution rate of 3-6 tablets.

TABLE 24

| | | 10 min | 15 min | 20 min | 30 min |
|---|---|---|---|---|---|
| Comparative Example 5 | Initial | 87.6 | 95.4 | 96.7 | 99.0 |
| | 40° C. closed bottle 1 month | 60.2 | 70.3 | 77.8 | 87.2 |
| Example 1 | Initial | 98.4 | 101.5 | 102.7 | 103.8 |
| | 40° C. closed bottle 1 month | 95.8 | 100.5 | 102.3 | 103.8 |

TABLE 24-continued

|  |  | 10 min | 15 min | 20 min | 30 min |
|---|---|---|---|---|---|
| Example 2 | Initial | 83.6 | 101.0 | 103.8 | 104.0 |
|  | 40° C. closed bottle 1 month | 84.0 | 98.4 | 103.3 | 104.5 |
| Example 3 | Initial | 51.9 | 92.1 | 96.4 | 99.1 |
|  | 40° C. closed bottle 1 month | 58.3 | 94.3 | 96.8 | 98.8 |

As shown in Table 24, it has been shown that the tablet of the present invention is superior in the dissolution property pioglitazone both before and after storage.

Experimental Example 4

The dissolution property of compound (I) in the tablets of Example 1, Example 2 and Example 3 was evaluated by the Paddle Method (50 rpm) using 0.3 M hydrochloric acid-potassium chloride buffer (37° C., pH 2.0, 900 mL). The results are shown in Table 25. In the Table, each value shows an average value of the dissolution rate of 3 tablets.

TABLE 25

|  |  | 10 min | 15 min | 20 min | 30 min |
|---|---|---|---|---|---|
| Example 1 | Initial | 98.4 | 98.7 | 98.8 | 98.9 |
|  | 40° C. closed bottle 1 month | 102.3 | 102.4 | 102.5 | 102.6 |
| Example 2 | Initial | 85.5 | 100.8 | 101.3 | 101.4 |
|  | 40° C. closed bottle 1 month | 79.3 | 99.1 | 99.8 | 100.6 |
| Example 3 | Initial | 81.8 | 92.2 | 97.3 | 99.5 |
|  | 40° C. closed bottle 1 month | 87.3 | 94.4 | 97.7 | 99.6 |

As shown in Table 25, it has been shown that the tablet of the present invention is superior in the dissolution property of compound (I) both before and after storage.

INDUSTRIAL APPLICABILITY

The solid preparation of the present invention is useful as a therapeutic drug for diabetes and the like and simultaneously has superior dissolution property, chemical stability and dissolution stability.

This application is based on application No. 2007-023594 filed in Japan, the contents of which are incorporated hereinto by reference.

The invention claimed is:

1. A multi-layered tablet comprising the following first and second layers:
   (1) the first layer comprising compressed granules comprising 2-[[6-[(3R)-3-amino-1-piperidinyl]-3,4-dihydro-3-methyl-2,4-dioxo-1(2H)-pyrimidinyl]methyl]-benzonitrile or a salt thereof and, as a first excipient, sugar or sugar alcohol; and
   (2) the second layer comprising compressed granules comprising pioglitazone or a salt thereof and, as a second excipient, lactose.

2. The multi-layer tablet of claim 1, wherein the first excipient sugar or sugar alcohol is lactose, sucrose, erythritol or mannitol.

3. The multi-layer tablet of claim 2, wherein the first excipient is mannitol.

4. The multi-layer tablet of claim 1, wherein the second layer comprises pioglitazone or a salt thereof, lactose and hydroxypropylcellulose.

\* \* \* \* \*

UNITED STATES PATENT AND TRADEMARK OFFICE
CERTIFICATE OF CORRECTION

PATENT NO. : 8,637,079 B2
APPLICATION NO. : 12/449255
DATED : January 28, 2014
INVENTOR(S) : Nakamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 491 days.

Signed and Sealed this
Second Day of June, 2015

Michelle K. Lee
*Director of the United States Patent and Trademark Office*